United States Patent [19]

Maas

[11] B 3,995,624

[45] Dec. 7, 1976

[54] INSTALLATION FOR THE PROCESSING OF EKG SIGNALS

[75] Inventor: Michael Maas, Erlangen, Germany

[73] Assignee: Siemens Aktiengesellschaft, Erlangen, Germany

[22] Filed: Dec. 19, 1974

[21] Appl. No.: 534,574

[44] Published under the second Trial Voluntary Protest Program on February 24, 1976 as document No. B 534,574.

[30] Foreign Application Priority Data

Dec. 22, 1973 Germany .......................... 2364312

[52] U.S. Cl. .......................................... 128/2.06 R
[51] Int. Cl.² ............................................ A61B 5/04
[58] Field of Search ................ 128/2.06 A, 2.06 F, 128/2.06 R, 419 PG

[56] References Cited
UNITED STATES PATENTS

| | | |
|---|---|---|
| 3,554,188 | 1/1971 | Lasch et al. ................... 128/2.06 F |
| 3,593,705 | 7/1971 | Thomas et al. ................ 128/2.06 A |
| 3,853,119 | 12/1974 | Peterson et al. .............. 128/2.06 R |
| 3,857,399 | 12/1974 | Zacouto ......................... 128/419 P |

*Primary Examiner*—William E. Kamm
*Attorney, Agent, or Firm*—Hill, Gross, Simpson, Van Santen, Steadman, Chiara & Simpson

[57] ABSTRACT

An installation for the processing of EKG signals, including a threshold element for the detection of the R-waves or displays in the EKG; and with a signal suppressor element which suppresses the EKG signal in the signal channel for a predetermined time period subsequent to each R-display being detected by the threshold element, wherein this time period is determined by the time span within which a condenser of an RC timing circuit, which has been charged to a predetermined initial voltage value prior to the incidence of the particular R-display, discharges to a lower cutoff voltage for the suppressor element.

2 Claims, 1 Drawing Figure

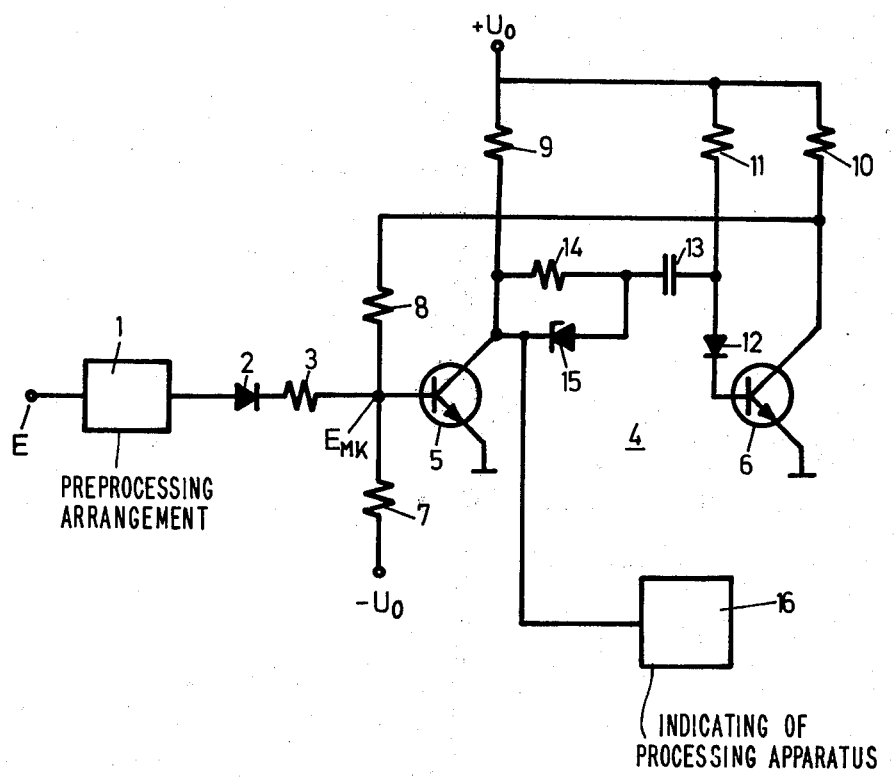

INSTALLATION FOR THE PROCESSING OF EKG SIGNALS

FIELD OF THE INVENTION

The present invention relates to an installation for the processing of EKG signals, including a threshold element for the detection of the R-waves or displays in the EKG; and with a signal suppressor element which suppresses the EKG signal in the signal channel for a predetermined time period subsequent to each R-display being detected by the threshold element, wherein this time period is determined by the time span within which a condenser of an RC timing circuit, which has been charged to a predetermined initial voltage value prior to the incidence of the particular R-display, discharges to a lower cutoff voltage for the suppressor element.

DISCUSSION OF THE PRIOR ART

In presently known installations of the above-mentioned type, the charging and discharging time-constants for the RC-timing circuit are so selected that, independently of the presently existent heart frequency, after the present occurrence of an R-display, the condenser always discharges within a discharging time period correspond to the heart refractive time at extremely high heart frequencies, for example, 200/minute, from a predetermined maximum peak voltage value (full charge) to the cutoff voltage value for the suppressor element, and subsequently recharges at a contrastingly much shorter charging time, to again its peak voltage value.

The selection of a discharge period for the timing circuit condenser which, independent of the presently existent heart frequency, correspondingly always constant remaining to the heart refractive period at extremely high heart frequencies, is disadvantageous since, as is known, the heart refractive time is not constant for different heart frequencies but displaces itself in conformance with the reduction in the heart frequency from shorter to longer time spans (as indicated experimentally, for example, at a heart frequency of 200/minute the heart refractive time consists in approximately 120 m sec and, in contrast therewith, at a heart frequency of 80/minute in approximately 160 m sec). This signifies that, for example, for frequencies within the normal range (approximately 60/minute to 120/minute), as well as for abnormally low heart frequencies (for example, 30/minute), the timing circuit condenser is each time always discharged prior to the completion of the actual refractive period and whereby, in an undesirable manner, the signal suppressor element is also presently switched off before completion of the particular refractive period which is significant for these heart frequencies. This may then have the result that components of the QRS-complex, for example, excessively high S-wave peaks, due to the too short suppressor time intervals will actuate the threshold element in an undesirable manner, and consequently be evaluated as genuine R-waves or displays. The above-described selection for the discharging time period is, however, much more disadvantageously effective in the reverse instance, meaning at extremely high heart frequencies, for example, at heart frequencies which lie far above 200/minute. In this case it may occur that, due to these high heart frequencies, the QRS-complexes follow so closely to each other so as to cause the occurrence of an R-display when the timing circuit condenser is still not fully discharged. Since these R-waves then presently fall within the suppressive time interval, they are not detected by the threshold element. An eventually subsequently connected in heart frequency measuring device will thereby erroneously indicate a heart frequency, which is cut in contrast with the actually existent heart frequency.

SUMMARY OF THE INVENTION

Accordingly, it is an object of the present invention to provide an installation of the above-mentioned type which is so constructed whereby the described disadvantages no longer can occur, which means, that the danger of double-counting at lower frequencies and the danger of a frequency curtailment at extremely high frequencies is avoided from the very beginning.

The foregong object is inventively attained in that the RC-timing circuit, relative to a heart frequency which does not exceed a median normal heart frequency value of, for example, 80/minute, is set at two part-sections of the pause interval between two successively following R-displays so that, during the first part-section, the condenser of the timing circuit is presently discharged from its fully-charged condition to the cut-off voltage value for the suppressor element and, during the second part-section, is subsequently again charged to its full charge voltage, wherein the first part-section is selected in a value which approximately corresponds to the refractive period of the heart at the selected heart frequency, and the second part section is the remaining pause interval.

In the installation according to the invention, in contrast to the commonly known installations, the charge and discharge time period of the timing circuit condenser is no longer constant for all heart frequencies. These times vary automatically much more in dependence upon the respectively presently heart frequency. If the heart frequency is located within the median normal range, for example, at 80/minute or therebelow, then the condenser is practically always fully charged to the predetermined voltage peak value, and also again fully discharged therefrom. The charge and discharge periods of the condenser are thus presently at a maximum for this heart frequency. Hereby, the suppression time period for the signals, corresponding to the longer heart refractive period at these frequencies, is also at a maximum. If, in contrast thereto, there is an increase in the heart frequency then, at increasing heart frequency values, the condenser is always less extensively charged. The charge and discharge periods shorten in a detrimental manner so that the signal suppressive time period, which correspond to the shorter heart refractive periods for these higher heart frequencies, are also shortened. Accordingly, in the inventive installation, the signal suppressive time period automatically correlates itself with the heart refractive periods which are significant to the different heart frequencies. The danger of a frequency doubling at low heart frequencies due to too short suppressive time periods, as well as a frequency halving or curtailment at extremely high heart frequencies due to excessively lengthy suppressive time periods is thus eliminated to an appreciable extent.

BRIEF DESCRIPTION OF THE DRAWING

Further advantages of the invention may now be ascertained from the following description of an exemplary embodiment thereof, taken in conjunction with the single FIGURE of the accompanying drawing which illustrates a schematic block circuit diagram of the inventive installation.

DETAILED DESCRIPTION

Referring now in detail to the schematic block diagram shown in the drawing, through the use of electrodes located, for example, on the body of a patient, EKG signals tapped-out therewith are transmitted to the input E of a preprocessing arrangement 1. The preprocessing arrangement 1 thereby includes, for example, a preamplifier for the EKG signals, a band-pass for the selection of frequencies, for example, which are significant for the QRS-complexes and, upon occasion, also an amplitude-compensating regulatory circuit for the R-display amplitudes. The EKG signals which are received at the output of the preprocessing arrangement are then transmitted, through a diode 2 having a series-connected ohmic resistance 3, to the input $E_{MK}$ of a monostable flip-flop or stepping oscillator 4.

The monostable flip-flop 4 hereby includes two transistors 5 and 6. The transistor 5 is herewith connected on its base side, on the one hand, to a negative operative voltage $-U_o$ (for example, $-15$ volt) through an ohmic resistance 7, and, on the other hand, connected through a ohmic resistance 8 with the collector of the transistor 6. Both transistors 5 and 6 further are each connected through, respectively, a collector resistance 9 or 10 with a positive operating voltage $+U_0$ (for example, $+15$ volts). Correspondingly applicable is also the base resistance 11 which is coupled to the base of the transistor 6 through a diode 12. Additionally coupled to the input of the diode 12 the oscillating condenser 13 of the monostable flip-flop 4. The operative connection of this oscillating condenser 13 to the collector of the transistor 5 is effected, on the one hand, across a high-ohmic series resistance 14, as well as, on the other hand a zener diode 15 which is connected in parallel thereto. The element 16 represents an indicating or processing apparatus for the collector output impulses of the transistor 5.

In the monostable flip-flop 4 as shown in the figure of the drawing, the transistor 5 provides a threshold element for the R-displays or waves of the EKG signals which come from the preprocessing arrangement. The transistor 5 herewith is controlled into a conductive condition at each occurrence of that kind of R-display. With a conductive transistor 5, the condenser 13 now discharges through the base resistance 11 of the transistor 6, as well as through the diode 15 and the conductive collector-emitter section of the transistor 5, for so long from a predetermined initial voltage value, until there has been reached the operating voltage for the diode 12, as well as for the base-emitter diode of the transistor 6. The transistor 6 hereby becomes conductive while the transistor 5 is blocked. During the time interval until the incidence of the subsequent R-display at the input of the transistor 5, the condenser 13 now charges through the collector resistance 9, as well as through the series resistance 14, to a new voltage value.

In the monostable flip-flop 4, the condenser 13 is now so dimensioned in its capacitive value, as well as the resistances 9, 11 and 14 in their resistance values, so that at a heart frequency of approximately 80/minute, the condenser 13 is charged to approximately to the voltage $U_o$ (voltage peak value) during the blocking phase of the transistor 5, and for conductive transistor 5 is corresponding again fully discharged from this peak value. The discharge time period, at this frequency, hereby consists of approximately 160 msec., and the charge period of approximately 590 msec. This discharge time period of approximately 160 msec. hereby essentially corresponds to the refractive period of the heart which is significant for this heart frequency value of 80/minute. If the heart frequency increases, then the condenser 13 is no longer charged to its full voltage value. The voltage charge of the condenser 13 becomes much lower with an increasing heart frequency. Correspondingly, there also shorten the charge and discharge periods of the condenser 13. This signifies that also the time period of the unstable phase of the monostable flip-flop 4 is displaced to lower values at an increasing heart frequency. Thus, if for example, the condenser 13 evidences a capacitive value of approximately 0.5 $\mu F$, and the resistance 9 is selected at approximately 15 k$\omega$, the resistance 11 at approximately 470 k$\omega$, and the resistance 14 at approximately 350 k$\omega$, then there is obtained, for example, at a heart frequency of 200/minute, a time period for the unstable phase of the flip-flop 4 of approximately 120 msec. This corresponds to approximately the refractive period of the heart at this high frequency. In the installation according to the FIGURE, the duration of the unstable phase of the flip-flop, as desired, automatically correlates with that of the heart refractive periods which are significant to the different heart frequencies. Frequency doubling due to a too short suppression time periods at low frequencies, as well as frequency halving or curtailment due to excessively lengthy suppression time periods at extremely high heart frequencies, can thus no longer occur from the very beginning thereof. The diode 15 in the discharge circuit of the condenser 13 is hereby preferably represented by a zener diode so that, at extremely high heart frequencies, for initiating the measurement the condenser 13 may be charged extremely rapidly at least once to its maximum value. The zener voltage of the zener diode 15 is herewith located with approximately 9 to 10 volts and may thereby be easily exceeded by the positive operating voltage of the monostable flip-flop of 15 volts which has been applied the first time for initiation of the measurement.

While there has been shown what is considered to be the preferred embodiment of the invention, it will be obvious that modifications may be made which come within the scope of the disclosure of the specification.

What is claimed is:

1. In an installation for the processing of EKG signals, including a threshold element for detecting R-displays in the EKG; a signal suppressor element for suppressing the EKG signal in the signal channel for a predetermined time period after each R-display detected by said threshold element, said signal suppressor element comprising a monostable flip-flop including two capacitively reactively connected transistors, one said transistor forming said threshold element for the R-displays of said EKG signals, said last-mentioned transistor having a collector resistance, said flip-flop having a condenser charged to a predetermined initial voltage value preceding the incidence of the respective R-display through the collector resistance of the blocked threshold element transistor, said suppressive time period being determined by the time span within which said flip-flop condenser discharges to a lower cutoff voltage value for said flip-flop through a base resistance of the other transistor and through the collector-emitter section of the threshold element transistor responsive to the latter being controlled into a conductive condition upon the incidence of the R-display, the improvement comprising: a high-ohmic resistance relative to the collector resistance of the threshold element transistor being connected in series in the charging path of said flip-flop condenser for increasing the charging time constants of said flip-flop condenser to a value so that, at heart frequencies not exceeding a median normal heart frequency value of about 80/min, the charging time period for a full condenser charging essentially corresponds to the time differential between R-display spacings and the refractive period of the heart at the selected heart frequency; and a diode bridging said high-ohmic resistance for discharging said condenser during said refractive period.

2. Installation as claimed in claim 1, said diode comprising a zener diode.

* * * * *